United States Patent [19]

Seltzman et al.

[11] Patent Number: 4,714,619
[45] Date of Patent: * Dec. 22, 1987

[54] AMINOMALONYL ALANINE COMPOUNDS AS DIETARY SWEETENERS

[75] Inventors: Herbert H. Seltzman, Raleigh; Yung-Ao Hsieh, Durham, both of N.C.

[73] Assignee: Research Triangle Institute, N.C.

[*] Notice: The portion of the term of this patent subsequent to Jan. 14, 2003 has been disclaimed.

[21] Appl. No.: 893,551

[22] PCT Filed: Sep. 18, 1985

[86] PCT No.: PCT/US85/01764
§ 371 Date: May 19, 1986
§ 102(e) Date: May 19, 1986

[87] PCT Pub. No.: WO86/01690
PCT Pub. Date: Mar. 27, 1986

[51] Int. Cl.$^4$ .......................... A23L 1/236; A23L 2/38
[52] U.S. Cl. .................................. 426/548; 426/590; 562/561; 560/169
[58] Field of Search .............................. 426/548, 590; 260/112.5 R; 560/169; 562/561

[56] References Cited

U.S. PATENT DOCUMENTS 4,564,548 1/1986 Seltzmann ........................... 426/548

Primary Examiner—Raymond N. Jones
Assistant Examiner—Carolyn Paden
Attorney, Agent, or Firm—Cushman, Darby & Cushman

[57] ABSTRACT

Compounds having relatively long shelf lives in acidic aqueous media and which are useful as sweeteners have the formula

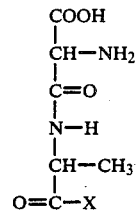

or are pharmaceutically acceptable salts thereof, wherein X is —OR or —NHR, or —NH$_2$, with R being alkyl having 3–10 carbon atoms.

7 Claims, 3 Drawing Figures

AMINOMALONYL ALANINE COMPOUNDS AS DIETARY SWEETENERS

FIELD OF THE INVENTION

This invention relates to new chemical compounds and to methods of using them as dietary sweeteners. In particular the invention also relates to compounds broadly classified as aminomalonyl D-alanine derivatives.

BACKGROUND OF THE INVENTION

Since the introduction of saccharin as an artificial sweetener, relative few new sweeteners have been developed. Among those that have been discovered, however, chief among them is the methyl ester of L-α-Aspartyl-L-phenylalanine, more commonly known as aspartame, disclosed in U.S. Pat. No. 3,492,131 to Schlatter. The viability of aspartame's use in non-dry applications is in serious question, however. Its recent introduction for use in soft drinks in this country was as a mixture with saccharin, the saccharin being used to maintain a sweet taste long after aspartame hydrolyzes to a non-sweet structure.

Thus, a non-toxic artificial sweetener compound comparable in sweetening ability to aspartame but which exhibits superior stability to aspartame in aqueous media would be a useful addition to the artificial sweeteners industry. Such compounds, compositions containing them, and methods of using these compounds as artificial sweeteners are the subject of the present invention.

Japanese Pat. No. 28068 (Takeda) describes aminomalonyl dipeptides which have a C-terminal amino acid of the L-configuration as sweetening compounds for preparing food. Surprisingly, we have found that such is not the case, but rather that the corresponding compounds of the present invention having a C-terminal amino acid of the D-configuration are sweet.

SUMMARY OF THE INVENTION

The present invention provides compounds useful as artificial sweeteners having the following structure:

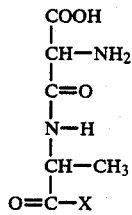

wherein X or —OR or —NHR, R being alkyl of 3–10 carbon atoms, or —NH$_2$. A preferred embodiment results when X or —OR and R is an isopropyl group, i.e. the isopropyl ester of aminomalonyl-D-alanine (herein also referred to simply as the "isopropyl ester"). Stereochemically, when synthesized the compounds of the present invention result as diastereomeric mixtures. The above formula is shown for convenience but it should be noted that the compounds will likely exist as zwitterions.

The pharmaceutically acceptable salts, such as the citrate, tartrate, hydrochloride, and phosphate, of the compounds disclosed herein are also effective as sweeteners. Such salts can be made using typical acids and procedures for making the salts are as conventionally known and practiced in the art.

The compounds of this invention generally range in sweetness between that of sucrose and aspartame. For example, the isopropyl ester of aminomalonyl alanine is 58 times sweeter than sucrose and about half as sweet as aspartame on a weight basis. Compared to saccharin, the isopropyl ester does not possess a "metallic" aftertaste, and there are virtually no detracting side tastes.

Additionally, the compound of this invention are believed to be non-toxic. Concerns have been raised regarding the principal metabolism products of aspartame—aspartic acid and phenylalanine. The former causes brain lesions in neonatal mice and the latter has been reported to induce grand mal-type seizures in monkeys, produce birth defects in pregnant women with phenylketonuria, induce behavioral changes, and alter brain chemistry. Saccharin itself is well known as a weak mutagen in the Ames assay, a property which is associated with carcinogenic potential.

In addition to the compounds having the structure given above, the invention also provides a method of sweetening a beverage, comprising dissolving a sufficient amount of at least one of the compounds disclosed herein to effect said sweetening.

It is therefore an object of this invention to provide an artificial sweetener.

It is further an object of this invention to provide an artificial sweetener which is relatively stable in aqueous solution.

It is further an object of this invention to provide an artificial sweetener which is non-toxic.

These and other objects and advantages of the invention will become more apparent and more readily appreciated from the following detailed description of presently preferred exemplary embodiments of the invention taken in conjunction with the accompanying FIGURE which is a diagrammatic representation of the synthesis of DL-aminomalonyl-D-alanine isopropyl ester. The lower case letter designations refer to the following:

a. Benzyl chloroformate (Z—Cl), NaHCO$_3$
b. NaOH, aq. EtOH
c. DBU, Benzyl bromide
d. tetramethylguanidine (TMG), aq. tetrahydrofuran (THF)
e. DCC, HOBt, dimethylformamide (DMF), D-alanine isopropyl ester (6)
f. 10% Pd/C, H$_2$, MeOH.

DETAILED DESCRIPTION

The synthesis of compounds within the scope of this invention will be described. This description is strictly for purposes of illustration, not limitation.

I. Synthesis of DL-aminomalonyl-D-alanine isopropyl ester.

Figure 1:
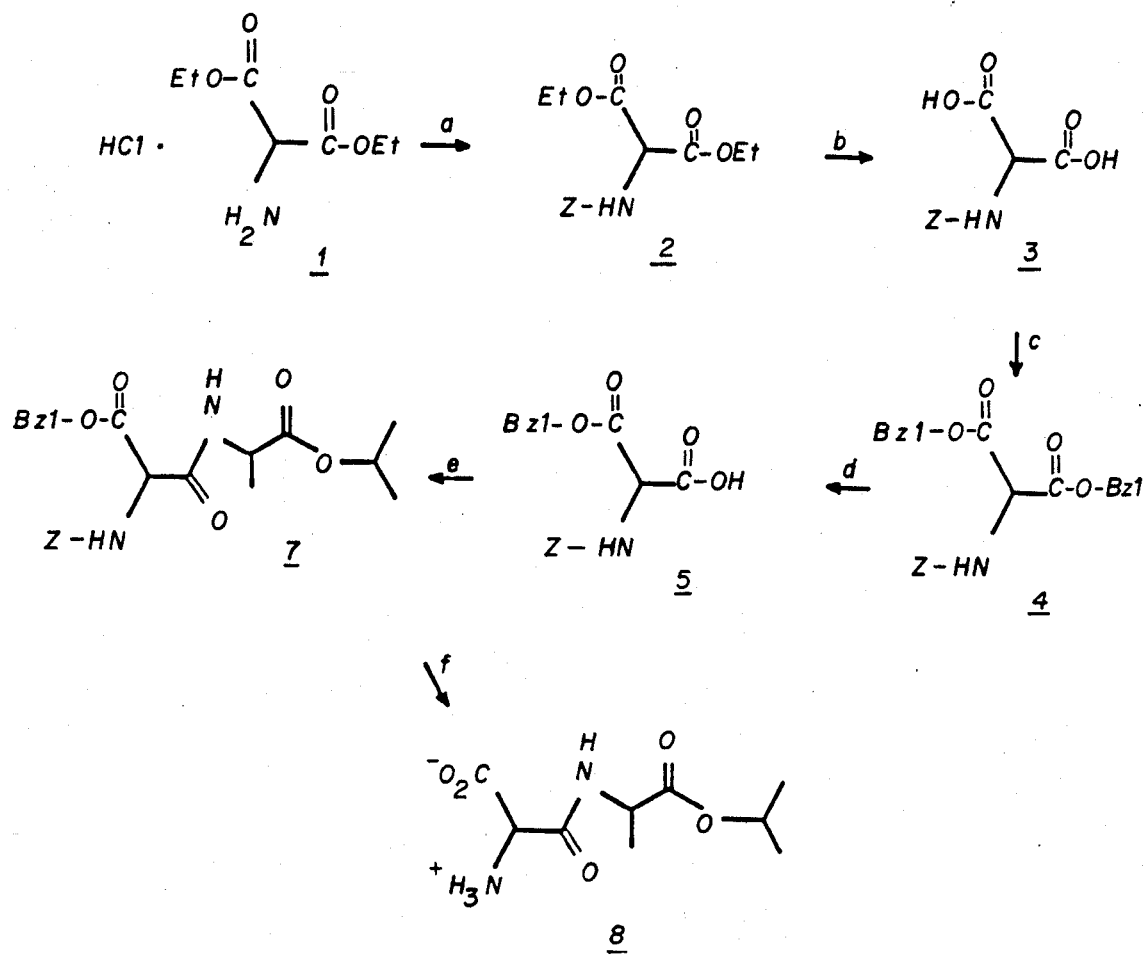
FIG. 1 is a flow chart illustrating the synthesis of DL-aminomalonyl-D-alanine isopropyl ester.
Figure 1:
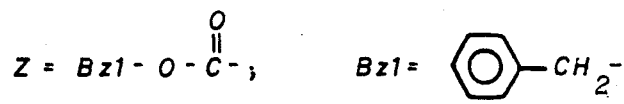

As an overview of the synthetic methods employed, the synthesis of DL-aminomalonyl-D-alanine isopropyl ester is shown in FIG. 1 and is now briefly summarized. Commercially available aminomalonic acid diethyl ester hydrochloride 1 was treated with Z-Cl (Z is an abbreviation for a benzyloxycarbonyl group) and NaHCO$_3$ to afford the N-protected Z-Ama-(OEt)$_2$ 2 (Ama=aminomalonyl group; Et=ethyl). Saponification provided the free acid 3. Treatment with excess benzyl bromide and 1,8-diazabicyclo[5.4.0]undec-7-ene (DBU) yielded the diester 4 which upon partial saponification provided the monobenzyl ester 5.

Coupling of 5 with D-alanine isopropyl ester 6 to afford the protected dipeptide 7 was achieved by standard dicyclohexylcarbodiimide (DCC) mediated procedures employing either hydroxybenzotriazole (HOBt) or N-hydroxysuccinimide (HOSu) as catalysts. The yields with either catalyst were comparable (70–80%), with the latter allowing easier removal of the reaction solvent (THF vs DMF) required for solubility reasons.

The final step in the sequence, removal of the benzyloxycarbonyl (Z) and benzyl (Bzl) moieties by hydrogenolysis over 10% Pd on carbon in methanol was followed by recrystallization from methanol to afford DL-aminomalonyl-D-alanine isopropyl ester.

Intermediates 2, 4, 5, and 6 are known compounds. The conversion of 4 to 5 using tetramethylguanidine is also believed to be novel.

Detailed procedural steps may be described as follows.

N-Benzyloxycarbonyl-aminomalonic Acid Diethyl Ester (2)

This compound was prepared according to the procedure of M. Fujino et al, Chem. Pharm. Bull. Japan, 24 (9), 2112 (1976), in which it was reported as an oil. The present inventors crystallized the crude oil from ether-petroleum ether in a dry ice-acetone bath, with scratching, to yield 5.13 g (83%); mp 37°–38° C.; 60 MHz nmr(CDCl$_3$, ppm) 1.25 (6H, t, J=7 Hz, CH$_3$CH$_2$—), 4.20 (4H, q, J=7 Hz, CH$_3$CH$_2$—), 5.03 (2H, s, ArCH$_2$—), 5.66 (1H, broad s, amide H), 7.23 (5H, s, ArH$_5$).

N-Benzyloxycarbonyl-aminomalonic Acid (3)

Compound 2 (3.49 mmol, 1.08 g) was dissolved in 3 mL 95% ethanol and treated with 3.49 mL 2N NaOH. The clear, colorless solution was left at room temperature for 19 hours until no starting material could be detected by tlc on silica gel (benzene:ethyl acetate, 4:1). Ethanol was evaporated under reduced pressure at room temperature. The aqueous solution was washed once with ether and then acidified with concentrated HCl to pH 2.5. The milky solution was extracted with ethyl acetate (3x). The pooled extract was washed with brine, dried over anhydrous Na$_2$SO$_4$ and evaporated to dryness. The product was crystallized from ether to yield 0.852 g of compound 3; mp 144°–145° C.; homogeneous by the tlc on silic gel (CHCl$_3$:methanol:acetate acid, 5:13:1); 250 MHz nmr (acetone-d$_6$, ppm) 5.00 (1H, d, J=8 Hz, α—H), 5.10 (2H, s, ArCH$_2$—), 6.84 (1H, d, J=8 Hz, amide H), 7.36 (5H, m, ArH$_5$). In a 60 MHz spectrum run in low water content acetone, a 9.7 ppm (2H, broad s, exchangeable with D$_2$O) was also observed.

N-Benzyloxycarbonyl-DL-aminomalonic Acid Monobenzyl Ester (5)

Compound 3 (4.55 mmol, 1.25 g) was dissolved in a mixture of 8 mL tetrahydrofuran (THF) and 8 mL CH$_3$CN. Benzyl bromide (9.88 mmol, 1.18 mL) and 1,8-diazabicyclo[5.4.0]undec-7-ene (DBU) (N. Ono et al., Bull. Chem. Soc, Japan, 51, 2401, 1978; C. G. Rao, Org. Prep. Proc. Int., 12, 225, 1980) (9.88 mmol, 1.48 mL) were added. The clear, colorless solution was left at room temperature overnight. The solution was concentrated under reduced pressure to half of the original volume. The product was precipitated by addition of water. The white crystalline material was collected by filtration, dried and triturated with petroleum ether to yield compound 4; 1.72 g (80%); mp 109°–110° C.; 250 MHz nmr (CDCl$_3$, ppm), 5.11, 5.16, 5.2 (7H, s, m, 3 ArCH$_2$— and α—H), 5.82 (1H, d, J=8 Hz, NH), 7.30 (15H, m, 3 ArH$_5$).

Z-Ama(OBzl)$_2$ (1.78 g, 4 mmol) was dissolved in 18 mL THF. TMG (0.5 mL, 4 mmol, freshly distilled) in H$_2$O was added. The clear colorless solution give a pH of 12.5–13.5 (pH hydrion paper). After 3 h at room temperature the pH went down to 8.5. The solution was evaporated under reduced pressure to remove THF. The cloudy solution was diluted with more water and extracted with ether. The aqueous phase was acidified to pH 2 with concentrated HCl. The cloudy aqueous phase was extracted with EtOAc (3×). The pooled EtOAc extract was washed with H$_2$O, dried over Na$_2$SO$_4$ and evaporated to dryness to give a white solid. The crude product was recrystallized from MeOH—H$_2$O. Yield: 1.17 g (86%), m.p. 118°–120° C., tlc on silica gel [CHCl$_3$:MeOH:HOAc=45:5:1] indicated the absence of 3 and 4. 250 MHz nmr (acetone-d$_6$, ppm). 5.06 (1H, d, partially overlapped with 5.1 peak, α—H), 5.1 (2H, s, ArCH$_2$—), 5.24 (2H, s, ArCH$_2$'—), 7.0 (1H, broad s, amide H), 7.35 (10H, m, 2 ArH$_5$).

N-Benzyloxycarbonyl-DL-aminomalonyl(benzyl ester)-D-alanine Isopropyl Ester (7)

N-Benzyloxycarbonyl-DL-aminomalonic acid monobenzyl ester 5 (0.156 g, 0.455 mmol) was dissolved in 1.5 mL DMF. The solution was cooled to −15° to −20° and then treated with DCC (94 mg, 0.455 mmol) and 1-hydroxybenzotriazole hydrate (62 mg, 0.46 mmol). The reaction mixture was stirred at −15° to −20° for 30 minutes. D-Alanine isopropyl ester hydrochloride (69 mg, 0.46 mmol) was then introduced, followed by the addition of N-methylmorpholine (50 microliters, 0.46 mmol). The reaction mixture was stirred at −15° to −20° C. for 1.5 hr, at 0° for 1 hr and 8 hr at room temperature. The reaction mixture was filtered to remove DCU and the filtrate was evaporated to dryness under high vacuum. The oily residue was taken up in EtOAc and the cloudy EtOAc solution was filtered. The EtOAc filtrate was then washed with 0.1N HCl (3×), H$_2$O (3×), 0.1N NaOH (3×), H$_2$O (3×), dried over anhydrous Na$_2$SO$_4$ and evaporated to dryness to give a clear oil. TLC on silica gel (benzene:EtOAc=4:1 and toluene:EtOAc=9:1) each indicated 3 spots; yield 0.187 g (91%). The crude material (0.167 g) was dissolved in CHCl$_3$, mixed with approximately 0.2 g of silica gel and loaded on a 12 g silica gel column in toluene. The crude product was then chromatographed by gradient elution with toluene to toluene:EtOAc=8:1. The major fraction (0.124 g) was identified by nmr as the desired product. The product was dissolved in a minimum amount of warm EtOAc; the solution was then diluted with an equal volume of ether and refrigerated. A white solid was obtained: mp 125°-130°, 250 MHz nmr (CDCl$_3$, ppm), 1.23 (m, 7.5H, (CH$_3$)$_2$—CH—O— overlapping with β—CH$_3$ of Ala of one of the 2 diastereomers), 1.37 (d, 1.5H, J=6.98 Hz, β—CH$_3$ of Ala of the second diastereomer, 4.45 (m, 1H, α—H of Ala), 5.00 (m, 1H, α—H of isopropyl), 5.12 (s, 2H, Ar—CH$_2$—), 5.18-5.34 (m, 3H, Ar—CH$_2$—O— of the benzyl ester overlapping with α—H of Ama), 7.33 (s, 10H, 2 ArH$_5$).

A 30 mmol scale preparation following the above procedure through the extraction step afforded the crude product which was crystallized from 2-propanol to give 8.91 g of tlc homogeneous 7. Another 2.17 g (total yield 81%) of 7 was obtained from the mother liquor by the above column chromatographic procedure.

Anal. Calcd for C$_{24}$H$_{28}$N$_2$O$_7$: C, 63.46; H, 6.18; N, 6.14; Found: C, 63.15; H, 6.04; N, 6.06.

DL-Aminomalonyl-D-Alanine Isopropyl Ester (8)

N-Benzyloxycarbonyl-DL-aminomalonyl(monobenzyl ester)-D-alanine isopropyl ester 7 (1.16 g, 2.53 mmol) was hydrogenated at room temperature in 100 mL MeOH over 0.573 g of 10% Pd/C at 40 psi in a Parr apparatus for 1 hr. The solution was then filtered through a Celite pad to remove the catalyst; the filtrate was concentrated under reduced pressure and the free dipeptides were precipitated from the solution by addition of ether. The crude product was recrystallized from MeOH. Yield 0.411 g (60%), mp 102°-104°, 250 MHz nmr (CD$_3$OD, ppm) 1.25 (m, 6H, (CH$_3$)$_2$CH—O—), 1.41 (2d, 3H, β—CH$_3$ of Ala), 4.38 (2q, 1H, α—H of AlA), 4.99 (m, 1H, α—H of isopropyl).

Anal. Calcd for C$_9$H$_{16}$N$_2$O$_5$: C, 46.55; H, 6.95; N, 12.06; Found C, 46.53; H, 6.95; N, 12.11.

L-Alanine Iopropyl Ester Hydrochloride (9)

L-Alanine (10 g, 0.112 mole) was suspended in 250 mL 2-propanol. Hydrogen chloride gas was bubbled into the solution. The temperature of the solution gradually rose to above 70° C. as hydrogen chloride was dissolved in the alcohol. After 2½ h, most of the free amino acid went into solution; more 2-propanol was added in small portions (approximately 30-50 mL) until a clear solution was obtained. The solution was left at room temperature overnight. The solution was evaporated through a NaOH trap under reduced pressure. The residue was dissolved in 100 mL 2-propanol and again evaporated to dryness. The residue was dried under high vaccum and a white mass was obtained, which was triturated with ether and collected by filtration to yield 16.4 g (96%), mp 84°-87° C. The crude product was recrystallized from CH$_3$CN—ether: mp 89°-90° C.; nmr (CD$_3$OD, ppm), 1.28 (d, J=6 Hz, 6H, CH$_3$ of isopropyl), 1.51 (3H, d J=8 Hz, β—CH$_3$), 3.98 (1H, q, J=7 Hz, Ala α—H), 4.7 (3H, broad s, amino H), 5.0 (1H, m, O—CHMe$_2$). The D-isomer was similarly prepared.

N-Benzyloxycarbonyl-D-alanine trans-2-Methylcyclohexyl Ester (10)

N-Benzyloxycarbonyl-D-alanine (2.5 mmol. 0.556 g) and trans-2-methylcyclohexanol (3 equivalents, 1 mL) were dissolved in 7 mL THF at room temperature, followed by the addition of 70 mg 4-dimethylaminopyridine. DCC (2.5 mmol, 0.515 g) was then introduced with stirring. The solution turned cloudy immediately and was stirred at room temperature overnight. The reaction mixture was stirred for another 15 min after several drops of HOAc were added to it. Dicyclohexylurea (DCU) was filtered off and the filtrate evaporated to dryness. The residue was dissolved in ethyl acetate. The EtOAc solution was filtered, washed with 0.5N HCl (2×), brine (2×), 5% NaHCO$_3$ (2×) and finally brine (2×). The organic phase, after being dried over anhydrous Na$_2$SO$_4$, showed one UV-positive tlc spot. A second spot, which could only be detected by phosphomolybdic acid (PMA)—Ce(SO$_4$)$_2$ spray, was identified as the unreacted alcohol by tlc comparison with authentic material. The ethyl acetate solution was evaporated to dryness and dried under high vacuum, giving a clear oil weighing 0.965 g. The crude material was chromatographed on a Merck Si—60 size C prepacked column by gradient elution with toluene to toluene:ethyl acetate (9:1). After evaporation, 0.629 g (72.0%) of clear, colorless oil was recovered: nmr (CDCl$_3$, ppm), 0.85-2.05 (13H, m, aliphatic H of cyclohexanol), 0.9 (3H, d, J=6 Hz, CH$_3$) 1.3 (3H, d, J=7 Hz, obscured by other aliphatic protons, β—CH$_3$ of Ala), 4.3 (2H, m, CH—O— and α—H), 5 (2H, s, ArCH$_2$—), 5.25 (1H, broad s, amide H), 7.15 (5H, s, ArH$_5$).

N-Benzoyloxycarbonyl-D-alanine Fenchyl Ester (11)

N-Benzyloxycarbonyl-D-alanine (8.646 g, 38.7 mmol) was dissolved in 150 mL THF and treated with DCC (7.987 g, 38.7 mmol) and 15 g of fenchyl alcohol (2.5 eq), followed by 4-dimethylaminopyridine (1.1 g). The reaction mixture was stirred at r.t. overnight. Several drops of HOAc were added and after 30 min DCU was filtered off. The filtrate was evaporated to dryness under reduced pressure and the oily residue was dissolved in EtOAc. The solution was refrigerated and more DCU was filtered off. The EtOAc solution was washed with 0.1N HCl (3×), H$_2$O, 0.1N NaOH (3×), H$_2$O (3×) and dried over Na$_2$SO$_4$. The solution was then evaporated to dryness under reduced pressure. The crude oily product so obtained was subjected to sublimation at 60° C./0.8 mm for 5 hours until the weight of the crude product was approximately 12-13 g. The oil was crystallized from hexane: yield 9.75 g (70%). Tlc (reverse phase C-18 plate, MeOH:H$_2$O=8:1) showed a single PMA—Ce(SO$_4$)$_2$ positive spot, m.p. 97°-98°. An analytical sample was recrystalized from ether, m.p. 98°-99°, 250 MHz nmr (CDCl$_3$, ppm) 0.76 (s, 3H, fenchyl 1-methyl), 1.04 (s, 3H, fenchyl 3-methyl), 1.08 (s, 3H, fenchyl 3-methyl), 1.12-1.79 (m, 7H, fenchyl aliphatic protons), 1.40 (d, 3H, J=7.35 Hz, β—CH$_3$ of Ala), 4.24 (q, 1H, J=7.35 Hz, α—H of Ala), 4.35 (d, 1H, J=1.8 Hz, α—H of fenchyl alcohol). Anal. Calcd for C$_{21}$H$_{19}$NO$_4$: C, 70.16; H, 8.13; N, 3.89; Found C, 70.05; H, 7.98; N, 3.78.

D-Alanine Fenchyl Ester Hydrochloride (12)

Crystalline N-benzyloxycarbonyl-D-alanine fenchyl ester (9.1 g, 25.3 mmol) was hydrogenated in 120 mL absolute MeOH and 22 mL 1.25N HCl/ether over 1.64 g of 10% Pd/C at 38 psi for 30 min in a Parr apparatus. The catalyst was removed by filtration through a Celite pad and the filtrate evaporated to dryness under reduced pressure. The salt was crystallized from ether. Yield: 5.68 g (86%) in 2 crops. mp 180°-181°, 250 MHz nmr (acetone-d$_6$, ppm) 0.85 (s, 3H fenchyl 1-methyl), 1.08 (s, 3H, fenchyl 3-methyl), 1.11 (s, 3H, fenchyl 3- methyl), 1.14–1.89 (m, 7H, fenchyl aliphatic protons), 1.74 (d, 3H, J=7.35 Hz, β—CH$_3$ of Ala), 4.35 (q, J=7.35 Hz, α—H of Ala), 4.43 (2S, 1H, α—H of fenchyl alcohol).

D-Alanine trans-2-Methylcyclohexyl Ester p-Toluenesulfonate (13)

N-Benzyloxycarbonyl-D-alanine-trans-2-methylcyclohexyl ester (14.7 g, 47.5 mmol) and p-toluenesulfonic acid monohydrate (9.04 g, 47.5 mmol) were dissolved in 135 mL MeOH. The methanolic solution was hydrogenated over 2.51 g of 10% Pd/C at 40 psi in a Parr apparatus for 1 hour. The catalyst was removed by filtration through a Celite pad and the filtrate was concentrated under reduced pressure. The salt was precipitated by addition of ether. Yield: 13.8 g in 2 crops (81%) mp 145°–147°. Tlc on silica gel (CHCl$_3$:MeOH:-HOAc=45:5:1) indicated a single ninhydrin positive spot. 250 MHz nmr (CD$_3$OD, ppm) 0.92 (d, 3H, J=6.25 Hz, trans-2-methyl), 1.09–1.99 (m, 7H, aliphatic cyclohexyl protons), 1.53 (2d, 3H, β—CH$_3$ of Ala), 2.37 (s, 3H, CH$_3$—Ar—SO$_3$H), 4.09 (2q, 1H, J=7.35 Hz, 2.57 Hz; α—H of Ala), 4.51 (m, 1H, α—H of alcohol); 7.22, 7.69 (ABq, 4H, J=8.46 Hz, CH$_3$—ArH$_4$—SO$_3$H).

N-Benzyloxycarbonyl-D-alanine 1-Adamantyl Ester (14)

N-Benzyloxycarbonyl-D-alanine (11.15 g, 50 mmol) was dissolved in 250 mL THF and treated with DCC (10.3 g, 50 mmol), 1-adamantanol (7.7 g, 51 mmol) and 1.45 g of 4-dimethylaminopyridine. The reaction mixture was stirred at room temperature. At the end of 24 hours, a few drops of HOAc was added and the reaction mixture was stirred for an additional 15 minutes. DCU was filtered off, the filtrate was evaporated to dryness under reduced pressure. The oily residue so obtained was dissolved in EtOAc and the solution was refrigerated overnight. More DCU was filtered off. The filtrate was then washed with 0.1N HCl (3×), H$_2$O (3×), 0.1N NaOH (3×), H$_2$O (3×) and dried over anhydrous Na$_2$SO$_4$. The solution was evaporated to dryness to give a clear oil. The oil was subjected to sublimation at 100°/0.1 mm for 5 hours. The oily residue was crystallized from hexane: mp 72°–74°, yield 11.6 g (75%), 250 MHz nmr (CDCl$_3$, ppm) 1.37 (d, 3H, J=7.35 Hz, β—CH$_3$ of Ala), 1.65 (s, 6H, adamantyl aliphatic protons of C's 4, 6 and 10), 2.09 (s, 6H, 1-adamantyl aliphatic protons of C's 2, 8 and 9), 2.16 (s, 3H, 1-adamantyl aliphatic protons of C's 3, 5 and 7), 4.23 (m, 1H, α—H of Ala), 5.09 (s, 2H, Ar—CH$_2$—O—), 5.32 (br.d, 1H, amide proton), 7.33 (s, 5H, ArH$_5$).

D-Alanine 1-Adamantyl Ester Hydrochloride (15)

N-Benzyloxycarbonyl-D-alanine 1-adamantyl ester (7.35 g, 20.6 mmol) was dissolved in 100 mL MeOH and 14.5 mL 1.25N HCl/ether. The solution was hydrogenated over 1.09 g of 10% Pd/C at 40 psi in a Parr apparatus at room temperature for 40 minutes. The solution was filtered through a Celite pad and the clear filtrate was evaporated to dryness to give a yellow oil, which was crystallized from EtOAc. A light yellow salt (4.2 g) was obtained. The crude product was recrystallized from MeOH-EtOAc; yielded 7.85 g (72%), mp 218°–219° (dec), 250 MHz nmr (CD$_3$OD, ppm) 1.50 (d, 3H, J=7.35 Hz, β—CH$_3$ of Ala), 1.72 (m, 6H, 1-adamantyl aliphatic protons of C's 2, 8 and 9), 2.18 (m, 9H, adamantyl aliphatic protons), 3.95 (q, 1H, J=7.35 Hz, α—H of Ala).

N-Benzyloxycarbonyl-DL aminomalonyl(benzyl ester)-D-alanine Fenchyl Ester (16)

N-Benzyloxycarbonyl-DL-aminomalonic acid monobenzyl ester (6.86 g, 20 mmol) was dissolved in 40 mL DMF and cooled to −20° C. DCC (4.12 g, 20 mmol) and 1-hydroxybenzotriazole hydrate (HOBt.H$_2$O) (2.70 g, 20 mmol) were then added. The reaction mixture was stirred at −20° C. for 30 minutes. D-Alanine fenchyl ester hydrochloride (5.23 g, 20 mmol) was added, followed by the addition of N-methylmorpholine (2.2 mL, 20 mmol). It was stirred at −20° to 15° C. for 1.5 hour, 0° C. for 2 hours and r.t. overnight. Several drops of HOAc were added and the reaction mixture was stirred for an additional 30 minutes. After DCU was removed by filtration, the filtrate was evaporated under high vacuum to dryness. The oil so obtained was dissolved in EtOAc and the solution was refrigerated. More DCU was filtered off. The EtOAc solution was extracted with H$_2$O (2×), 0.1N HCl (3×), H$_2$O (3×), 0.1N NaOH (3×) and H$_2$O (3×). The organic phase was dried over Na$_2$SO$_4$ and evaporated to dryness. The oil was crystallized from hexane. Yield 2.81 g, mp 71°–75° C., tlc on silica gel (benzene:EtOAc=9:1), single spot (Cl$_2$+o-tolidine spray). Another 5.16 g of the product was isolated by chromatographing the mother liquor (crude weight=8.32 g) on a column 360 g of silica gel using toluene: EtOAc=7:1 as the eluant (overall yield=72.5%). 250 MHz nmr (CDCl$_3$, ppm), 0.74 and 0.76 (2 s, 3H, diastereomeric, fenchyl 1-methyl), 1.02 and 1.04 (2 s, 3H, diastereomeric fenchyl 3-methyl), 1.10 and 1.11 (2 s, 3H, diastereomeric fenchyl 3-methyl), 1.18–1.73 (m, 7H, fenchyl aliphatic protons), 1.43 (d, 3H, J=7.0 Hz, β—CH$_3$ of Ala, partially overlapped with fenchyl aliphatic protons), 4.55 (q, 1H, J=7.0 Hz, α—H of Ala, 4.97 (2br s, 1H, α—H of fenchyl), 5.12 (s, 2H, Ar—CH$_2$—), 5.18–5.37 (m, 3H, Ar—CH$_2$ overlapped with α—H of Ama), 6.03 (br d, 1H, amide proton), 6.83 and 7.04 (2 br d, 1H, urethane H), 7.33 (s, 10H, 2 ArH$_5$).

N-Benzyloxycarbonyl-DL-aminomalonyl(benzyl ester)-L-alanine Isopropyl Ester (17) (intermediate for comparative non-sweet isomers)

This compound was prepared by the same DCCHOBt procedure as described for the D-alanine isomers on a 30 mmol scale. The crude product was crystallized from 2-propanol and 7.25 g of tlc homogeneous material (on silica gel toluene:EtOAc=4:1) was collected. The filtrate, showing 4 spots on tlc in the same solvent system was chromatographed on silica gel by gradient elution with toluene to toluene:EtOAc=5:1. The major fraction collected was crystallized from 2-propanol; yielded 2.76 g in 3 crops; overall yield 10.0 g (73%), mp 130°–133°. 250 MHz nmr (CDCl$_3$, ppm) 1.23 (m, 7.5 H, (CH$_3$)$_2$CH—O— overlapping with β—CH$_3$ of Ala of one of the 2 diastereomers), 1.37 (d, 1.5H, β—CH$_3$ of Ala of the second diastereomer), 4.45 (m, 1H, α—H of Ala), 5.0 (m, 1H, α—H of isopropyl), 5.12 (s, 2H, Ar—CH$_2$ of Z). 5.18–5.34 (m, 3H, Ar—CH$_2$—O overlapping with α—H of Ala), 6.02 (br d, H, amide H) 6.85 (br d, 1H, urethane H), 7.33 (s, 10H, 2 ArH$_5$). Anal. Calcd for C$_{24}$H$_{28}$N$_2$O$_7$: C, 63.15; H, 6.18; N, 6.14; Found C, 62.98; H, 6.21; N, 5.96.

N-Benzyloxycarbonyl-DL-aminomalonyl(benzyl ester)-D-alanine trans-2-Methylcyclohexyl Ester (18)

N-Benzyloxycarbonyl-DL-aminomalonic acid monobenzyl ester (0.343 g, 1 mmol) was dissolved in 4 mL THF and cooled to −15° to −20°. DCC (0.206 g, 1 mmol) and N-hydroxysuccinimide (0.115 g, 1 mmol) were then added. The reaction mixture was stirred in the cold for 30 minutes. D-Alanine trans-2-methylcyclohexyl ester p-toluenesulfonate (0.358 g, 1 mmol) was then suspended in the solution, followed by the addition of Et$_3$N (0.14 mL, 1 mmol). The reaction mixture was stirred at −15° to −20° for 2.5 hours, 0° for 1 hour and room temperature overnight. A drop of HOAc was added. The reaction mixture was stirred for an additional 15 minutes. After DCU was removed by filtration, the filtrate was evaporated to dryness to give a clear oil. A white crystalline material was obtained when the oil was triturated with water; yield 0.55 g; tlc on silica gel (toluene:EtOAc=4:1) gave 4 spots. The crude product was purified on 25 g silica gel by gradient elution with toluene to toluene:EtOAc=5:1. The major fraction collected was identified by nmr as the desired dipeptide. The oil was crystallized by trituration in hexane: yield 0.391 g, mp 116°-119°, 250 MHz nmr (CDCl$_3$, ppm) 0.87 (2d, 3H, 2-methyl), 1.04-1.11 (m, 9H, cyclohexyl aliphatic protons), 1.22 and 1.40 (m, 3H, β—CH$_3$ of the 2 diastereomeric Ala overlapping with cyclohexyl aliphatic protons), 4.45 (m, 2H, α—H's of cyclohexanol and Ala), 4.95-5.29 (m, 3H, α—H of Ama and Ar—CH$_2$ of benzyl ester), 5.12 (s, 2H, Ar—$\overline{CH_2}$— of Z), 6.03 (br.d, 1H, urethane H), 6.81, 6.98 (br $\overline{d}$, 1H, amide H), 7.32 (s, 10H, 2 Ar—H$_5$).

N-Benzyloxycarbonyl-DL-aminomalonyl(benzyl ester)-D-alanine 1-Adamantyl Ester (19)

This compound was prepared by the known dicyclohexylcarbodiimide-hydroxysuccinimide (DCCDOSu) procedure as described for the preparation of compound (18) above on a 20 mmol scale. Acetonitrile was the solvent for this coupling. The crude product (11.2 g) was purified on a 600 g silica gel column by gradient elution with toluene to toluene:EtOAc=9:1. The crude oil so obtained was crystallized by scratching in hexane in an ice-water bath: yielded 8.66 g (79%). 250 MHz nmr (CDCl$_3$, ppm) 1.19 (d, 1.5H, β—CH$_3$ of Ala of one of the two diastereomers, J=7.35 Hz), 1.35 (d, 1.5H, β—CH$_3$ of Ala of the second diastereomer J=6.98 Hz), 1.62 (s, 6H, adamantyl aliphatic protons of C's 4, 6 and 10), 2.07 (s, 6H, adamantyl aliphatic protons of C's 2, 8 and 9), 2.16 (s, 3H, adamantyl aliphatic protons of C's 3, 5 and 7), 4.23 (m, 1H, α—H of Ala), 5.09 (s, 2H, Ar—$\overline{CH_2}$—O— of Z), 5.17-5.30 (m, 3H, Ar—$\overline{CH_2}$—O— benzyl ester overlapping with α—H of Ama), 7.32 (s, 10H, 2 ArH$_5$).

DL-Aminomalonyl-L-alanine Isopropyl Ester (20) (comparative non-sweet isomers)

This compound was prepared by the procedure as described for the D-alanine isomers. The crude product was recrystallized from MeOH: yield 83.5 mg (68%), mp 108°-109°, 250 MHz nmr (CD$_3$OD, ppm) 1.25 (m, 6H, ($\overline{CH_3}$)$_2$CH—O), 1.39 (m, 3H, β—CH$_3$ of Ala), 4.38 (2q, 1$\overline{H}$, α—H of Ala), 4.99 (m, 1H, α—H of isopropyl).

Anal. Calcd for C$_9$H$_{16}$N$_2$O$_5$: C, 46.55, H, 6.95; N, 12.06; Found C, 46.18; H, 7.02; N, 12.11.

DL-Aminomalonyl-D-alanine Fenchyl Ester (21) (sweet)

This compound was prepared by the procedure as described for the isopropyl ester analog. The crude product was recrystallized from MeOH—H$_2$O: yield 0.513 g (67.5%), 250 MHz nmr (CD$_3$OD, ppm) 0.80 (m, 3H, fenchyl 1—CH$_3$), 1.06 (m, 3H, fenchyl 2—CH$_3$), 1.46 (m, 3H, β—CH$_3$ of Ala), 4.37 (m, 1H, α—H of Ala), 4.51 (m, 1H, α—H of fenchyl alcohol).

Calcd for C$_{16}$H$_{26}$N$_2$O$_5$: C, 58.88; H, 8.03; N, 8.58; Found C, 58.38; H, 8.21; N, 8.38.

DL-Aminomalonyl-D-alanine 1-Adamantyl Ester Citrate (22) (sweet)

N-Benzyloxycarbonyl-DL-aminomalonyl-(benzyl ester)-D-alanine 1-adamantyl ester (0.523 g, 0.955 mmol) and citric acid (0.414 g, 0.955 mmol) were dissolved in 11 mL MeOH and hydrogenated over 54 mg 10% Pd/C at 40 psi for 7-10 minutes. The methanolic solution was then filtered through a Celite pad to give a colorless filtrate, which was concentrated to 2-3 mL and precipitated with ether: yield 0.350 g (73%), mp 108°-112°, 250 MHz nmr (CD$_3$OD, ppm) 1.39 (m, 3H, β—CH$_3$ of Ala), 1.71 (s, 6H, adamantyl aliphatic protons of C's 4, 6 and 10), 2.13 (s, 9H, adamantyl aliphatic protons), 2.72, 2.92 (2d, 4H, —$\overline{CH_2}$—COOH), 4.32 (m, 1H, α—H of Ala). Nmr indicated 2 moles of the dipeptides combine with 1 mole of citric acid.

Calcd for C$_{38}$H$_{56}$N$_4$O$_{17}$: C, 54.28; H, 6.71; N, 6.66; Found, C, 54.55; H, 7.00; N, 6.80.

DL-Aminomalonyl-D-alanine trans-2-Methylcyclohexyl Ester Citrate (23) (sweet)

N-Benzyloxycarbonyl-DL-aminomalonyl-(benzyl ester)-D-alanine trans-2-methylcyclohexyl ester (99.8 mg, 0.195 mmol) was dissolved in 6 mL MeOH and hydrogenated over 10.5 mg of 10% Pd/C at atmospheric pressure for 7 minutes until no more H$_2$ was consumed. The solution was filtered through a Celite pad and the colorless filtrate was evaporated to dryness under reduced pressure to give a white foam. The crude product was quickly dissolved in 6 mL EtOH and citric acid (37.5 mg; 0.195 mmol) was added. The solution was evaporated to dryness to give a white mass. The crude product was recrystallized from EtOH-ether. The 60 MHz nmr spectrum of this compound indicated that 2 moles of the dipeptide combine with one mole of citric acid, mp 71°-75°. 250 MHz nmr (CD$_3$OD, ppm) of the free dipeptides: 1.11-1.92 (m, 9H, cyclohexanol aliphatic protons), 1.41 (d, 3H, β—CH$_3$, of Ala partially overlapping with the aliphatic protons, J=7.35 Hz), 4.12 (m, 2H, α—H of Ala and α—H of trans-2-methylcyclohexanol).

D-Alaninamide Hydrochloride (24)

D-Alanine methyl ester hydrochloride [M. Zaoral et al, Collection Czech, Chem. Commun., 32, 843 (1967)] is converted to the title amide following the procedure [R. W. Chambers and F. H. Carpenter, J. Am. Chem. Soc., 77, 1522 (1955)] reported for L-alaninamide hydrochloride [J. K. Chang et al, J. Med. Chem., 14, 484 (1971)].

N-Benzyloxycarbonyl-D-alanine Isopropyl Amide (25)

N-Benzyloxycarbonyl-D-alanine (2.232 g, 10 mmol) and HOBt hydrate (1.53 g, 10 mmol) are dissolved in 40 mL freshly distilled DMF and cooled in an ice-H$_2$O bath. DCC (2.06 g, 10 mmol) is added. The reaction mixture is stirred in the cold for 15 minutes, isopropylamine (0.85 mL, 10 mmol) is then introduced. It is stirred in the cold for 2 hours and room temperature overnight. HOAc (a few drops) is added and the reaction mixture stirred at room temperature for another 15 minutes. It is filtered to remove DCU and the filtrate layered with 50 mL EtOAc and 80 mL H$_2$O. The phases are separated and the aqueous phase is extracted with 50 mL EtOAc. The pooled EtOAc extract is wazhed with H$_2$O, 0.1N HCl (3×), H$_2$O (3×), 0.1N NaOH (3×), H$_2$O (3×), dried over anhydrous Na$_2$SO$_4$ and evaporated to dryness. The crude product is purified by liquid column chromatography on silica gel eluting with toluene/EtOAc mixtures.

D-Alanine Isopropyl Amide (26)

N-Benzyloxycarbonyl-D-alanine isopropyl amide (1.322 g, 5 mmol) is hydrogenated in 20 mL MeOH over 100 mg 10% Pd/C in a Parr Apparatus at 40 psi and room temperature until no more hydrogen is consumed. The methanolic suspension is filtered through a Celite pad to remove the catalyst and the filtrate is evaporated to dryness. The desired product is purified by conversion into a crystalline amino acid amide salt.

N-Benzyloxycarbonyl-D-alanine 1-Adamantyl Amide (27)

The title compound is prepared from N-benzyloxycarbonyl-D-alanine and 1-adamantanamine using the usual DCC-HOBt procedure described above.

D-Alanine 1-Adamantyl Amide (28)

N-Benzyloxycarbonyl-D-alanine 1-adamantyl amide is hydrogenated by the precedure as described for the isopropyl amide.

N-Benzyloxycarbonyl-DL-aminomalonyl(monobenzyl ester)-D-alanine-Isopropyl Amide (29)

N-Benzyloxycarbonyl-DL-aminomalonic acid monobenzyl ester (0.156 g, 0.434 mmol) is dissolved in 1.5 mL DMF. The solution is cooled to −15° to −20° and then treated with DCC (94 mg, 0.455 mmol) and 1-hydroxybenzotriazole hydrate (62 mg, 0.46 mmol). The reaction mixture is stirred at −15° to −20° for 30 minutes. D-Alanine-isopropyl amide hydrochloride (76 mg, 0.46 mmol) is then added followed by the addition of N-methylmorpholine (50 µl, 0.46 mmol). The reaction mixture is stirred at −15° to −20° for 1.5 hours, at 0° for 1 hour and at room temperature for 8 hours. The reaction mixture is filtered to remove DCU and the filtrate is freed of solvent under high vacuum. The residue is taken up in EtOAc and filtered. The EtOAc filtrate is then washed with 0.1N HCl (3×), H$_2$O (3×), 0.1N NaOH (3×), H$_2$O (3×), dried over anhydrous Na$_2$SO$_4$ and evaporated to dryness. The crude product is then chromatographed on silica gel by elution with tolucene/EtOAc mixtures. The product containing fraction as identified by nmr, is precipitated from EtOAc, MeOH and ether mixtures.

N-Benzyloxycarbonyl-DL-aminomalonyl-(monobenzyl ester)-D-alanine-1-Adamantyl Amide (30)

This compound is prepared by the usual DCC mediate procedure as described for the isopropyl analog. Acetonitrile and THF can also be employed as the solvent for this coupling. The crude product is purified on a silica gel column by elution with toluene/EtOAc mixtures. The product so obtained is crystallized from hexane or precipitation from EtOAc with ether or hexane.

N-Benzyloxycarbonyl-DL-aminomalonyl(monobenzyl ester)-D-alanamide (31)

N-Benzyloxycarbonyl-DL-aminomalonic acid monobenzyl ester (0.343 g, 1 mmol) is dissolved in 4 mL THF and cooled to −15° to −20°. DCC (0.206 g, 1 mmol) and N-hydroxysuccinimide (0.115 g, 1 mmol) are then added. The reaction mixture is stirred in the cold for 30 minutes. D-Alaninamide hydrochloride (0.124 g, 1 mmol) is then added followed by the addition of Et$_3$N (0.14 mL, 1 mmol). The reaction mixture is stirred at −15° to −20° for 2.5 hours, 0° for 1 hour and room temperature overnight. A few drops of HOAc is added. The reaction mixture is stirred for an additional 15 minutes. After DCU is removed by filtration, the filtrate is evaporated to dryness. The crude product is purified by chromatography on silica gel by elution with toluene/EtOAc mixtures. The fraction identified by nmr as the desired product is crystallized or precipitated from hexane, EtOAc, ether mixtures.

DL-Aminomalonyl-D-alaninamide (32)

N-Benzyloxycarbonyl-DL-aminomalonyl-(benzyl ester)-D-alaninamide (4.13 g, 10 mmol) is hydrogenated in 40 mL MeOH over 400 mg 10% Pd/C in a Parr apparatus at room temperature and 40 psi. Products are crystallized from alcohols-diethyl ether.

DL-Aminomalonyl-D-alanine Isopropyl Amide (33)

N-Benzyloxycarbonyl-DL-aminomalonyl-(benzyl ester)-D-alanine isopropyl ester is hydrogenated by the procedure described for the D-alaninamide analog. The product is similarly purified.

DL-Aminomalonyl-D-alanine 1-Adamantyl Amide (34)

This material is prepared by the same hydrogenolysis as described for the D-alaninamide analog.

II. Taste Test

Many artificial sweeteners do not have a pleasant sucrose-like taste that is free of detracting side tastes and after tastes. These compounds, including many of the peptides, exhibit side tastes such as being minty, or licorice-like, or are even bitter or medicine-like. Others exhibit after tastes such as a metallic taste. Still other sweeteners exhibit a lingering sweet taste. Unlike many artificial sweeteners, the isopropyl ester described in this taste test exhibits an uncommon sucrose-like sweet taste that is free of detracting side and after tastes. The isopropyl ester exhibits a rapid onset and a rapid decay of sweet taste, much like sucrose.

Following established methods a taste panel was set up and trained. The compound was tasted at concentrations of 0.021, 0.007 and 0.21% w/v (0.86, 3.0 and 9.0 mM) versus aspartame concentrations of 0.01, 0.03, 0.1 and 0.3% w/v (0.34, 1.0, 3.4 and 10 mM) and sucrose 2, 4, 9, 18 and 36% w/v (62, 125, 250, 500 and 1000 mM). The normalized averaged results for the isopropyl ester, sucrose and aspartame are given in Table 1 and shown graphically in FIG. 2.

Both the isopropyl ester and aspartame solutions were rated as sweet and pleasant by the taste panel. The relative potencies of the sweeteners are expressed as the reciprocal of the concentrations required for a score of 50 on the sweetness scale. Based on sucrose=1.0, the sweetness potency of of the preferred isopropyl ester would be 58 and that of aspartame would be 126 on a weight scale.

Since the potency response lines are approximately parallel, the above potency comparison method is valid.

III. Stability Studies

The most significant limitation of those few peptides here-to-fore reported that have good taste qualities is their poor stability in aqueous solution. Those peptides have carboxyl-terminal L-amino acid esters that require for sweetness that the ester is made from a small alkyl alcohol, most often methanol. Such peptide esters are especially labile to hydrolysis and cyclization in aqueous solution resulting in the generation of non-sweet products. However, the formation of peptide esters of hindered alcohols, such as isopropyl alcohol, for these carboxyl-terminal L-amino acid peptides results in peptide esters with much reduced or no sweet taste. Thus, for carboxyl-terminal L-amino acid dipeptide esters, sweet taste and poor stability in solution are related properties.

The unexpected discovery of the sweet taste of the carboxyl-terminal D-amino acid dipeptide ester, D,L-aminomalonyl-D-alanine isopropyl ester, provided an intense peptide ester sweetener exhibiting stability that is markedly superior to the prior art. For example, in pH 3.5 solution, the isopropyl ester showed less than 5% degradation after 36 days at ambient temperature while after the same period aspartame was more than 50% degraded to both more and less polar products. This ten fold improvement in stability is especially significant as regards its use in comparably acidic soft drinks. Furthermore, after 36 days in pH 7.4 buffer the isopropyl ester was 70% degraded while after only one-fourth that time (9 days) aspartame was 100% degraded. These results show that in the key issue of stability of peptide sweeteners, the isopropyl ester offers marked improvements relative to the prior art.

Stability was examined in aqueous solution at various pHs. Solutions (1% w/v) were prepared in 0.05M phosphate buffer adjusted to pH 7.4 and pH 3.5. Storage at ambient temperature over 36 days was monitored by hplc analysis (waters radial-pak reverse phase C-8 column, 25% $CH_3CN$, 0.05% $TFA/H_2O$ eluant, 210 nm U.V. detection). Aspartame was examined similarly for comparison purposes.

IV. Ames/Salmonella Mutagenicity Assay

The isopropyl ester was tested for mutuagenic potential in the Ames assay employing: (1) five Salmonella strains which detect frameshift mutagens or base-pair substitution mutagens, (2) both the presence and absence of mammalian S9 microsomal liver fraction as the metabolic activator, which differentiate promutagens from direct-acting mutagens, (3) five dose levels (3000, 300, 30, 3, 0.3 ug/plate), and (4) three plates per dose. The compound was also tested for toxicity, with and without S9 activation, at the two highest doses. The compound showed neither mutagenic potential nor toxicity for any of these tests. Positive controls and spontaneous background revertants were within acceptable ranges.

V. Acute Toxicity Testing

The isopropyl ester was evaluated for acute oral toxicity in Swiss male mice. The testing parameters were as follows: each test group contained six mice (20-30 grams each); the isopropyl ester was administered in an aqueous solution as a single oral dose of 100 mg/kg and 300 mg/kg; two solvent controls were also administered; the mice were again given food two hours after sample administration.

Body weights were measured on day $-3$, 0, $+7$ and $+14$. Physiological parameters were examined the entire first day, then three times a day through the first week and twice a day for the second week. Blood serum analyses for urea nitrogen and alanine aminotransferase activities were measured on day $-3$ and day $+14$. On day 14, a gross necropsy was performed on each mouse.

The results of this acute whole animal toxicity study indicated no toxic effect under the conditions tested. The toxicological parameters were all negative and no behavioral or pharmacological effects were observed. There was no excessive eating or drinking during the study. The weights of all test animals during the 14-day study were normal. No toxic effects were detected in the necropsy.

Blood samples were collected from the tail vein for biochemical testing of serum samples. This procedure virtually eliminated hemolyzed samples. Neither elevated serum urea nitrogen nor elevated alanine aminotransferase activity were detected in post-study samples from either the 100 mg/kg or the 300 mg/kg doses. These analyses demonstrated the absence of kidney and liver toxicity respectively.

Therefore the isopropyl ester appears to be nontoxic at all doses tested as determined by biochemical acceptance criteria as well.

TABLE 1

Taste Panel Results
Average Scores for Standard and Test Compounds[1]
Test Series: 4

| Compound | Concentration (Millimolar) | Sweet? | Bitter? | Salty? | Off Taste? | After Taste? | Pleasant? |
|---|---|---|---|---|---|---|---|
| Aspartame | 0.3392 | 15 | 0 | 1 | 1 | 1 | 4 |
| | | (7) | (0) | (1) | (1) | (1) | (2) |
| | 1.0194 | 27 | 0 | 3 | 4 | 2 | 15 |
| | | (5) | (0) | (3) | (3) | (1) | (8) |
| | 3.3979 | 68 | 4 | 2 | 2 | 26 | 26 |
| | | (4) | (3) | (1) | (2) | (7) | (10) |
| | 10.1937 | 83 | 0 | 1 | 4 | 34 | 9 |
| | | (6) | (0) | (1) | (4) | (14) | (18) |
| Sucrose | 62.0000 | 13 | 3 | 0 | 4 | 0 | −4 |
| | | (7) | (3) | (0) | (4) | (0) | (8) |
| | 125.0000 | 30 | 2 | 8 | 4 | 5 | 18 |
| | | (5) | (1) | (5) | (3) | (2) | (9) |
| | 250.0000 | 64 | 0 | 1 | 0 | 0 | 49 |

TABLE 1-continued

Taste Panel Results
Average Scores for Standard and Test Compounds[1]
Test Series: 4

| Compound | Concentration (Millimolar) | Sweet? | Bitter? | Salty? | Off Taste? | After Taste? | Pleasant? |
|---|---|---|---|---|---|---|---|
|  |  | (3) | (0) | (1) | (0) | (0) | (8) |
|  | 500.0000 | 75 | 6 | 12 | 5 | 7 | 32 |
|  |  | (4) | (5) | (9) | (3) | (3) | (11) |
|  | 1000.0000 | 97 | 0 | 1 | 0 | 30 | 26 |
|  |  | (2) | (0) | (1) | (0) | (13) | (20) |
| Isopropyl Ester | 0.8621 | 4 | 7 | 21 | 13 | 4 | −11 |
|  |  | (2) | (7) | (21) | (9) | (4) | (8) |
|  | 3.0172 | 32 | 3 | 5 | 2 | 6 | 13 |
|  |  | (8) | (3) | (5) | (2) | (4) | (8) |
|  | 9.0517 | 61 | 1 | 3 | 3 | 4 | 34 |
|  |  | (9) | (1) | (3) | (2) | (3) | (13) |

[1]The scores have been normalized to 100 and averaged.
The numbers in parentheses are standard error values.

VI. Comparative Taste Test

In order to demonstrate the significant distinction between the compounds of the present invention having the D-configuration and that of their isomer having the L-configuration, the following compounds were tested:
Sucrose
Aspartame
Compound (8)-D,L-Aminomalonyl-D-alanine Isopropyl Ester
Compound (21)-D,L-Aminomalonyl-D-alanine Fenchyl Ester
Compound (20)-D,L-Aminomalonyl-L-alanine Isopropyl Ester The compounds were dissolved in distilled water at the concentrations specified in Table 2. Solutions were made up and kept overnight in a refrigerator. The following day, they were poured into individual graduated plastic cups (10 ml per cup) and allowed to warm to room temperature. A taste panel was convened and testing begun that same day. Tasting and evaluation was done by the standard protocol developed by Dr. Robert Gesteland of Taste and Smell Consulting Group, Inc.

The first solution tasted (reference standard for the panel) was 0.25M sucrose. Other solutions were tasted in radomized fashion. The random order was arrived at as follows:

i. An ordered list of the compounds and concentrations was prepared (26 solutions in all).
ii. 0.25M sucrose was designated as 1.
iii. A standard table of random numbers was used in which the numbers were grouped as two-digit numbers. A point in the table was chosen at random (blind pointing). The first solution in the list was given the first random number in the sequence (read right-to-left, up-to-down) which is between 2 and 26. The second solution in the list was given the next random number in the sequence between 2 and 26, etc. Repeat numbers were ignored.
iv. Solutions were then labeled A (for number 1) B (for random number 2), C-Z.
v. Panelists were instructed to taste the solutions in alphabetical order.

With the assistance of Taste and Smell Consulting Group, Inc., taste panel members were trained adn tested for their ability to discriminate sucrose solutions of varying concentrations. In summary it may be stated that all 9 panel members had acceptble correlation scores. Their results were in good agreement with those which have been previously reported in siilar types of studies. For the test series the correlations for each panelist for sucrose and aspartame were acceptable as were the overall results obtained by averaging individual scores. The results of the taste panel are set forth in Table 2 wherein the parenthetical figures represent the standard error values for the number above.

Figure 2:
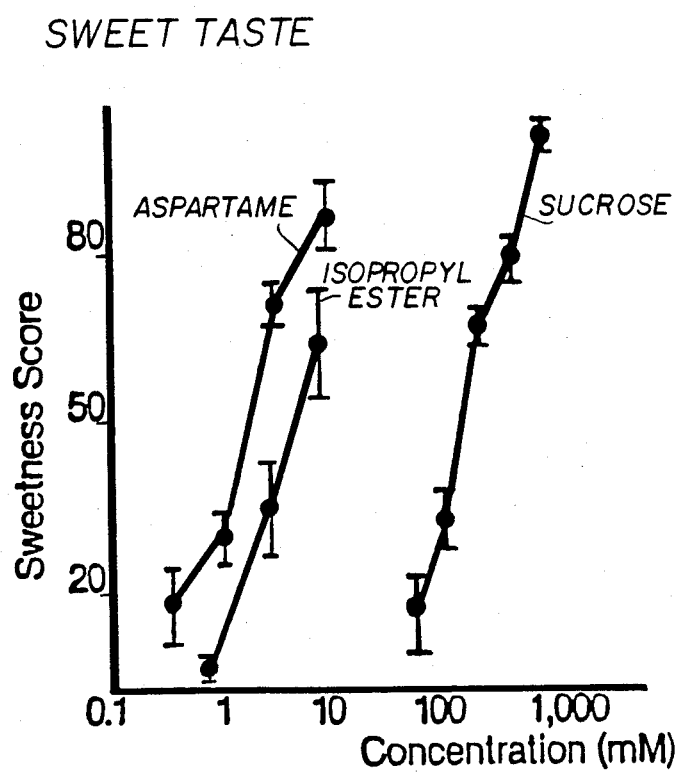
FIG. 2 is a graphical comparison of the sweetness potency of the isopropyl ester with sucrose and aspartame. Each data point represents the mean∓SEM.

Based on the results shown in Table 3, a dose response curve for sucrose, Compound (8) and Compound (20) and same is illustrated in FIG. 2.

Figure 3:
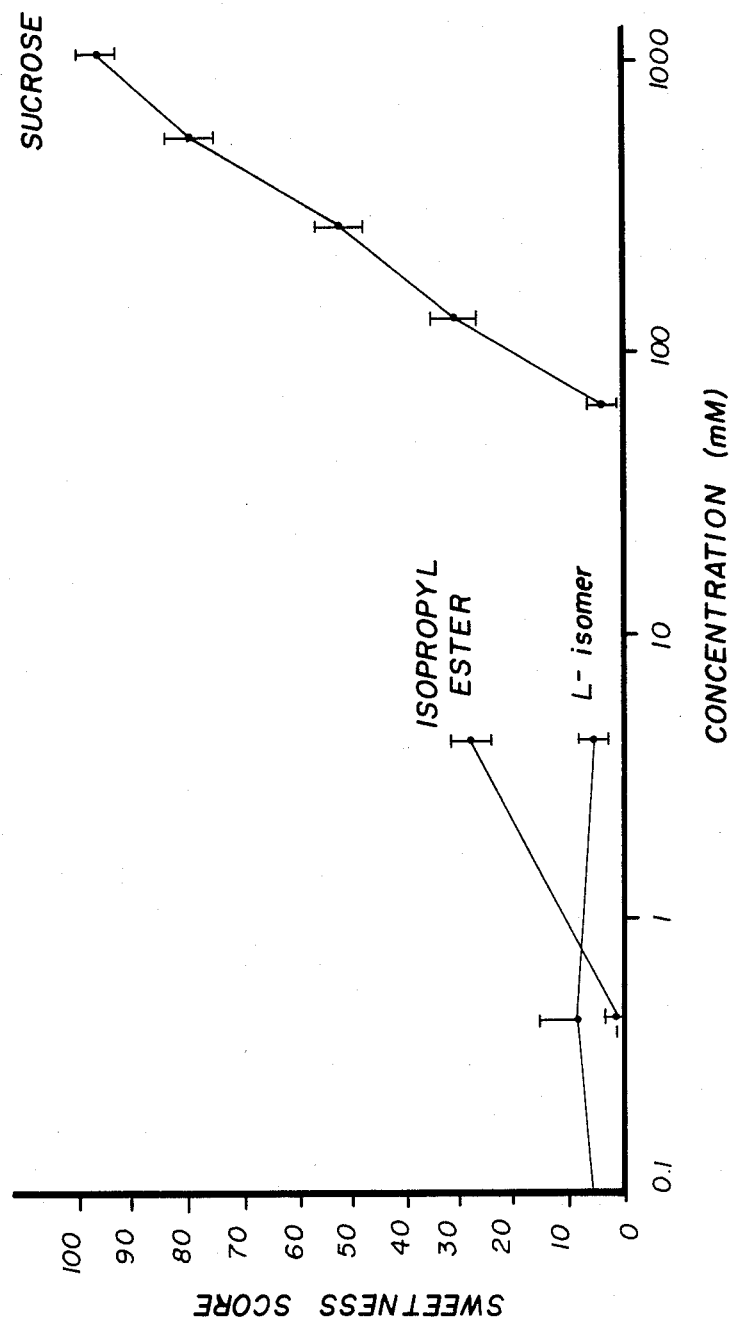
FIG. 3 is a graphical comparison of the sweetness potency of the D-isopropyl ester with the corresponding L-isopropyl ester and sucrose.

From a review of FIG. 3, as well as the results set forth in Table 2, it is clear that Compound (8) (the isopropyl ester of the D-configuration according to the present invention) is sweet, whereas the corresponding iosmer of the L-configuration, Compound (20), is not sweet.

Compounds (21), (22), and (23) were also found to be sweet.

TABLE 2

Comparative Taste Panel Results
Average Scores for Standard and Test Compounds

| Compound | Concentration (Millimolar) | Sweet? | Bitter? | Salty? | Off Taste? | After Taste? | Pleasant? |
|---|---|---|---|---|---|---|---|
| Aspartame | 0.3398 | 9 | 1 | 0 | 1 | 1 | 16 |
|  |  | (2) | (1) | (0) | (1) | (1) | (12) |
|  | 1.0194 | 27 | 3 | 10 | 6 | 7 | 8 |
|  |  | (5) | (2) | (5) | (3) | (3) | (9) |
|  | 3.3979 | 66 | 2 | 3 | 12 | 16 | 22 |
|  |  | (4) | (2) | (3) | (6) | (5) | (9) |
|  | 10.1937 | 64 | 5 | 0 | 17 | 22 | 12 |
|  |  | (10) | (3) | (0) | (9) | (10) | (19) |
| Sucrose | 62.0000 | 3 | 6 | 9 | 9 | 10 | 17 |
|  |  | (2) | (6) | (9) | (7) | (7) | (12) |
|  | 125.0000 | 30 | 2 | 1 | 3 | 4 | 21 |
|  |  | (4) | (2) | (1) | (1) | (2) | (8) |
|  | 250.0000 | 52 | 3 | 7 | 12 | 15 | 34 |

TABLE 2-continued

Comparative Taste Panel Results
Average Scores for Standard and Test Compounds

| Compound | Concentration (Millimolar) | Sweet? | Bitter? | Salty? | Off Taste? | After Taste? | Pleasant? |
|---|---|---|---|---|---|---|---|
|  |  | (4) | (2) | (7) | (6) | (7) | (9) |
|  | 500.0000 | 78 | 0 | 0 | 10 | 9 | 35 |
|  |  | (4) | (0) | (0) | (6) | (5) | (11) |
|  | 1000.0000 | 95 | 0 | 0 | 12 | 8 | 28 |
|  |  | (3) | (0) | (0) | (11) | (5) | (19) |
| (8) | 0.0431 | 2 | 1 | 1 | 2 | 0 | 15 |
|  |  | (2) | (1) | (1) | (2) | (0) | (12) |
|  | 0.4307 | 1 | 12 | 11 | 8 | 7 | 10 |
|  |  | (1) | (10) | (11) | (6) | (6) | (13) |
|  | 4.3066 | 28 | 0 | 12 | 3 | 5 | 24 |
|  |  | (4) | (0) | (12) | (2) | (3) | (13) |
| (21) | 0.0306 | 1 | 3 | 4 | 13 | 12 | −9 |
|  |  | (1) | (1) | (4) | (9) | (9) | (6) |
|  | 0.3064 | 8 | 29 | 9 | 56 | 50 | −57 |
|  |  | (5) | (9) | (6) | (12) | (13) | (14) |
|  | 3.0637 | 13 | 90 | 62 | 99 | 79 | −83 |
|  |  | (11) | (8) | (19) | (1) | (14) | (12) |
| (20) | 0.0431 | 3 | 9 | 3 | 5 | 0 | 14 |
|  |  | (2) | (8) | (3) | (4) | (0) | (13) |
|  | 0.4307 | 8 | 14 | 16 | 8 | 8 | 5 |
|  |  | (7) | (10) | (16) | (7) | (6) | (6) |
|  | 4.3066 | 5 | 0 | 0 | 5 | 5 | 19 |
|  |  | (2) | (0) | (0) | (3) | (4) | (12) |

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. Aminomalonyl-D-alanine derivatives having the formula:

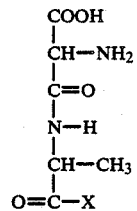

and pharmaceutically acceptable salts thereof, wherein X is —NHR or —OR with R being alkyl of from 3 to 10 carbon atoms, or —NH₂.

2. The derivative of claim 1, wherein R is isopropyl.

3. A composition of matter comprising the combination of at least one aminomalonyl-D-alanine derivative having the formula:

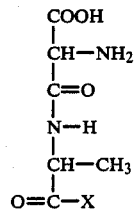

or pharmaceutically acceptable salts thereof, wherein X is —NHR or —OR with R being alkyl of from 3 to 10 carbon atoms, or —NH₂, dissolved in an aqueous medium.

4. The composition of claim 3, wherein R is isopropyl.

5. The composition of claim 3, wherein said aqueous medium is a beverage.

6. A method of sweetening a beverage, comprising dissolving therein at least one aminomalonyl-D-alanine derivative having the formula:

$$\begin{array}{c} \text{COOH} \\ | \\ \text{CH—NH}_2 \\ | \\ \text{C}=\text{O} \\ | \\ \text{N—H} \\ | \\ \text{CH—CH}_3 \\ | \\ \text{O}=\text{C—X} \end{array}$$

or pharmaceutically acceptable salts thereof, wherein X is —NHR or —OR with R being alkyl of from 3 to 10 carbon atoms, or —NH₂, said at least one compound being dissolved in an amount sufficient to effect said sweetening.

7. The method of claim 6, wherein R is isopropyl.

* * * * *